(12) United States Patent
Solomon (10) Patent No.: US 9,872,952 B2
(45) Date of Patent: Jan. 23, 2018

(54) SOFT DUAL-LAYER RECTAL SPECULUM

(76) Inventor: Deborah Solomon, Phoenix, AZ (US)

( * ) Notice: Subject to any disclaimer, the term of this patent is extended or adjusted under 35 U.S.C. 154(b) by 1137 days.

(21) Appl. No.: 13/176,260

(22) Filed: Jul. 5, 2011

(65) Prior Publication Data

US 2012/0004611 A1     Jan. 5, 2012

Related U.S. Application Data

(60) Provisional application No. 61/361,381, filed on Jul. 3, 2010.

(51) Int. Cl.
| | |
|---|---|
| *A61M 3/02* | (2006.01) |
| *A61B 1/015* | (2006.01) |
| *A61B 1/31* | (2006.01) |
| *A61B 1/32* | (2006.01) |

(52) U.S. Cl.
CPC ........... *A61M 3/0279* (2013.01); *A61B 1/015* (2013.01); *A61B 1/31* (2013.01); *A61B 1/32* (2013.01); *A61M 2210/1064* (2013.01)

(58) Field of Classification Search
CPC ............. A61B 1/31; A61B 1/32; A61B 1/015; A61M 3/0279
USPC ........ 604/275; 600/195, 201, 202, 205, 130, 600/138, 160; 606/197, 192, 193, 207
See application file for complete search history.

(56) References Cited

U.S. PATENT DOCUMENTS

| | | | | |
|---|---|---|---|---|
| 2,470,293 | A | * | 5/1949 | D Angelo .......... A61M 3/0279 422/255 |
| 3,071,129 | A | * | 1/1963 | Wasserman ............ A61B 1/015 600/156 |
| 3,132,645 | A | * | 5/1964 | Gasper ...................... A61B 1/31 600/184 |
| 3,417,746 | A | * | 12/1968 | Moore ................. A61B 1/2676 348/359 |
| 3,631,852 | A | * | 1/1972 | Hay ........................ A61B 1/303 600/184 |
| 3,779,233 | A | * | 12/1973 | Saslow et al. ................. 600/184 |
| 4,943,285 | A | * | 7/1990 | Hawks ................ A61M 3/0279 600/29 |
| 5,072,720 | A | * | 12/1991 | Francis et al. ................. 600/186 |
| 5,351,674 | A | | 10/1994 | Hawks |
| 5,722,983 | A | * | 3/1998 | Van Der Weegen ...................... A61B 1/00142 606/193 |

(Continued)

*Primary Examiner* — Matthew F Desanto
(74) *Attorney, Agent, or Firm* — Zeman-Mullen & Ford, LLP (57) ABSTRACT

A soft dual-layer rectal speculum includes a main tube member having a distal end for insertion into a patient's rectum and a proximal end for connection to a waste removal hose where at least a portion of the main tube member includes an inner hard layer and an outer soft layer, and an inlet tube member for directing fluids into the main tube member. The inlet tube member may include a swivel mechanism and the portion of the main tube member having an inner hard layer and an outer soft layer may include a measurement gauge that is visible through the outer soft layer but can't be felt through the outer soft layer. A rectal speculum assembly includes the soft dual-layer rectal speculum described above and an obturator which includes an elongated member having a tapered distal end capable of extending through the distal end of the main tube member. The tapered distal end of the obturator may be made of a soft, pliable material or an inner hard layer (or member) and an outer soft layer.

26 Claims, 6 Drawing Sheets

(56) References Cited

U.S. PATENT DOCUMENTS

| | | | |
|---|---|---|---|
| 5,795,289 A * | 8/1998 | Wyttenbach | 600/207 |
| 6,142,931 A * | 11/2000 | Kaji | 600/114 |
| 6,953,450 B2 * | 10/2005 | Baldwin et al. | 604/248 |
| 2002/0129443 A1 | 9/2002 | Di Cecco | |
| 2005/0090786 A1 * | 4/2005 | Moon | 604/275 |
| 2006/0020230 A1 | 1/2006 | Baxter-Jones et al. | |
| 2007/0073216 A1 * | 3/2007 | McAuliffe | A61M 3/0275 604/30 |
| 2007/0151565 A1 * | 7/2007 | Sanders Acedo | 128/839 |

* cited by examiner

SOFT DUAL-LAYER RECTAL SPECULUM

CROSS-REFERENCE TO RELATED APPLICATIONS

This application claims priority to provisional patent application having Ser. No. 61/361,381, filed Jul. 3, 2010, which is herein incorporated by reference in its entirety.

BACKGROUND OF THE INVENTION

The prior art includes numerous rectal speculums for use with colon hydrotherapy. Prior art rectal speculums for use with colon hydrotherapy are typically formed from a single piece of material. Conventional designs take the form of a hollow cylindrical tubular member having a distal end for insertion into a patient's rectum and a proximal end for connection to a waste discharge hose, and an inlet tube which intersects with the hollow cylindrical tubular member for directing fluid into the hollow cylindrical tubular member. The prior art speculums are usually formed of a rigid material that will not deform or flex when brought into contact with another body. As a consequence, the rectal speculum can often be easily felt by a patient during insertion, positioning, and use, thereby creating an uncomfortable feeling for the patient. In addition, a slight hand pressure on the hollow cylindrical tubular member can be magnified into a higher force at the distal tip of the hollow cylindrical tubular member that is inserted and positioned within a patient's rectum.

The prior art rectal speculums are inserted into a patient's rectum with the assistance of an obturator which typically includes an elongated member having a tapered end capable of extending through the distal end of the rectal speculum and a handle end for assisting in the insertion and removal of the obturator within the rectal speculum. Like the prior art rectal speculums, the obturators are formed form a single piece of rigid material that will not deform or flex when brought into contact with another body. As a result, a patient also feels the discomfort of the obturator during the insertion and placement of the rectal speculum.

Accordingly, the patient suffers greater pain and discomfort than necessary using prior art rectal speculums and obturators. Therefore, a need exists for a new and improved rectal speculum that is easy to position and use and that is also comfortable to the patient during placement and use. A need also exists for a new and improved obturator that can be easily used with the new and improved rectal speculum to further enhance a patient's comfort during the placement and use of the new and improved rectal speculum.

SUMMARY OF THE INVENTION

The present invention is directed to a soft dual-layer rectal speculum for use with colon hydrotherapy that includes a main tube member wherein at least a portion of the main tube member is comprised of an inner firm, or hard, layer and an outer soft layer which adheres to the inner hard layer and an inlet tube member intersecting the main tube member for directing fluids into the main tube member. The main tube member includes a distal end for insertion into a patient's rectum and a proximal end for connection to a waste removal hose. In addition, the diameter of the inlet tube member is smaller than the diameter for the main tube member.

The outer soft layer of the main tube member adheres to the inner hard layer of the main tube member and this adhesion may be formed by one or more of thermal bonding, chemical bonding, or mechanical bonding. In one exemplary embodiment of the soft dual-layer rectal speculum of the present invention, the inner hard layer and the outer soft layer of the main tube member are created by a two step molding process where the inner hard layer is molded first and the outer soft layer is molded second such that the outer soft layer adheres to the inner hard layer. The inner hard layer may comprise one or more of a polypropylene and synthetic resin and the outer soft layer may comprise one or more of a polyethylene, a silicone, a soft urethane, a thermoplastic elastomer, and a thermoplastic polyurethane.

In another exemplary embodiment of the soft dual-layer rectal speculum of the present invention, the outer soft layer of at least a portion of the main tube member is transparent. In still another exemplary embodiment of the soft dual-layer rectal speculum of the present invention, the portion of the main tube member that comprises an inner hard layer and an outer soft layer further comprises a measurement gauge that is visible through the outer soft layer. The measurement gauge may be imprinted within, or tooled into, the hard inner layer.

In yet another exemplary embodiment of the soft dual-layer rectal speculum of the present invention, the soft dual-layer rectal speculum further includes a thumb rest extending outward from an outer surface of the main tube member opposite the inlet tube member. The thumb rest may take one of many different forms including, but not limited to, a flange or bar member.

In another exemplary embodiment of the soft dual-layer rectal speculum of the present invention, the proximal end of the main tube member includes one or more ribs for securing the proximal end of the main tube member to a waste removal hose. In yet another exemplary embodiment of the soft dual-layer rectal speculum of the present invention, the inlet tube member includes a swivel mechanism capable of enabling a fluid line connected to the inlet tube member to rotate in relation to the main tube member.

The main tube member of the soft dual-layer rectal speculum of the present invention may comprise a distal portion located near the distal end of the main tube member and a proximal portion located near the proximal end of the main tube member. In use, most of the distal portion of the main tube member is inserted into a patient's rectum while the proximal portion of the main tube member remains external to the patient. In this exemplary embodiment, the distal portion of the main tube member includes an inner hard layer and an outer soft layer and the inlet tube member is located on the proximal portion of the main tube member near the proximal end of the main tube member. In another exemplary embodiment, the distance between the distal portion of the main tube member and the inlet tube member is at least greater than one half of the length of the distal portion of the main tube member to enable waste and fluid lines connected to the soft dual-layer rectal speculum to be further away from the patient during use.

Like the previously described exemplary embodiments, the outer soft layer of the distal portion of the main tube member adheres to the inner hard layer of the distal portion of the main tube member and this adhesion may be performed by one or more of thermal bonding, chemical bonding, or mechanical bonding. In addition, the exemplary embodiment of the soft dual-layer rectal speculum that includes a main tube member having a proximal portion comprising an inner hard layer and an outer soft layer may further include one or more of a transparent outer soft layer, a measurement gauge visible through a transparent outer soft layer, and a hard inner layer that is imprinted or tooled with a measurement gauge.

In yet another exemplary embodiment, the distal portion of the main tube member which includes an inner hard layer and an outer soft layer further includes an annular depression. In still another exemplary embodiment, the distal portion of the main tube member may further include annular expansions on opposite sides of the annular depression. Further, the inner hard layer may comprise one or more of a polypropylene and a synthetic resin and the outer soft layer may comprise one or more of a polyethylene, a silicone, a soft urethane, a thermoplastic elastomer, and a thermoplastic polyurethane.

The present invention is also directed to a rectal speculum assembly for use with colon hydrotherapy which includes a main tube member with at least a portion of the tube member having an inner hard layer and an outer soft layer and an inlet tube intersecting the main tube member for directing fluids into the main tube member, and an obturator removably positioned within the main tube member wherein the obturator includes an elongated member having a tapered distal end capable of extending through the distal end of the main tube member and a proximal end having a handle portion for assisting in the insertion and removal of the obturator within the main tube member. In one exemplary embodiment of the rectal speculum assembly, the tapered distal end of the obturator is made of a soft, pliable material. The soft pliable material may comprise one or more of polyethylene, silicone, soft urethane, thermoplastic elastomer, or thermoplastic polyurethane.

In another exemplary embodiment of the rectal speculum assembly, the tapered distal end of the obturator is made of an inner hard layer and an outer soft layer. The inner hard layer may comprise one or more of a polypropylene and a synthetic resin and the outer soft layer may comprise one or more of a polyethylene, a silicone, a soft urethane, a thermoplastic elastomer, and a thermoplastic polyurethane.

In yet another exemplary embodiment of the rectal speculum assembly, the elongated member of the obturator may include one or more stabilizing flanges.

BRIEF DESCRIPTION OF THE DRAWINGS

The subject invention will hereinafter be described in conjunction with the appended drawing figures, wherein like numerals denote like elements.

DETAILED DESCRIPTION OF EXEMPLARY EMBODIMENTS

The soft dual-layer rectal speculum and rectal speculum assembly of the present invention generally provide a rectal speculum and rectal speculum assembly that are both easy to position and use and that are also comfortable to a patient or client during placement and use. The soft dual-layer rectal speculum of the present invention includes an unobstructed main tube member with a distal end adapted to be inserted into a patient's rectum and a proximal end adapted to be connected to a waste removal hose and an inlet tube member that is connectable to a source of water or other treating fluid to permit injection of the fluid into the main tube member. At least a portion of the main tube member includes an inner hard layer and an outer soft layer.

Figure 1:
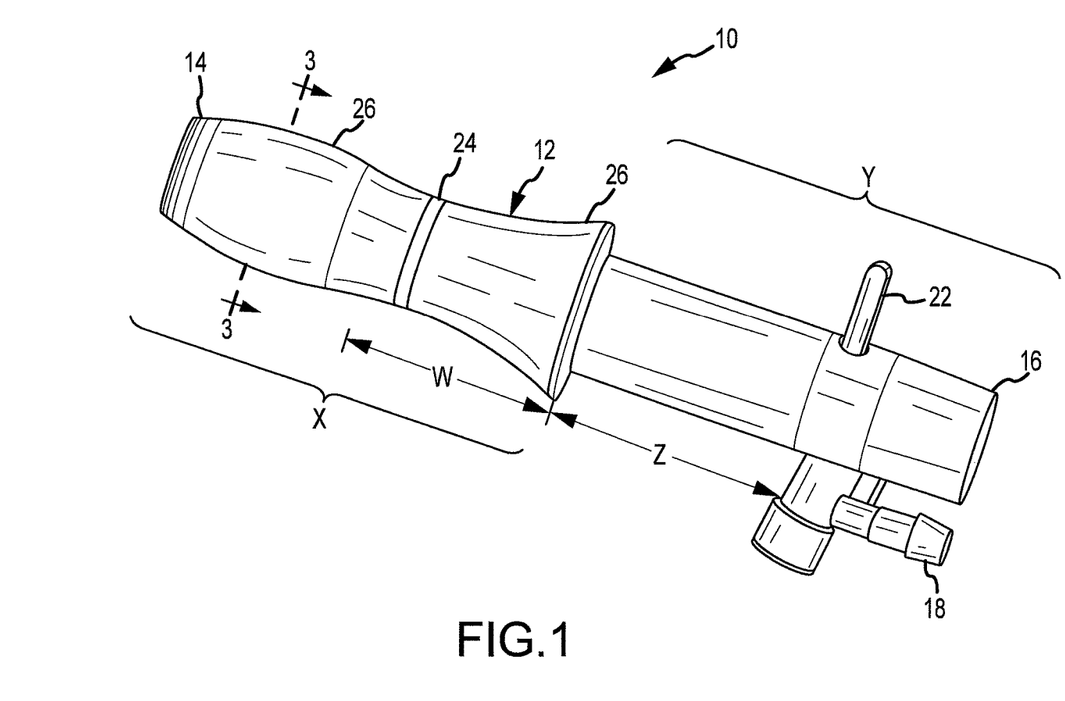
FIG. 1 is a perspective view of an exemplary embodiment of a rectal speculum in accordance with the present invention.

FIG. 1 is a perspective view of an exemplary embodiment of a rectal speculum 10 in accordance with the present invention. Rectal speculum 10 includes a main tube member 12 having a distal end 14 for insertion into a patient's rectum and a proximal end 16 for connection to a waste removal hose. At least a portion of the main tube member 12 includes an inner hard layer and an outer soft layer as further shown and described with reference to FIGS. 3-5. Rectal speculum 10 also includes an inlet tube member 18 for directing fluids into the main tube member 12.

Inlet tube member 18 intersects main tube member 12 near the proximal end 16 of main tube member 12 and inlet tube member 18 has a diameter that is smaller than the diameter of main tube member 12. Inlet tube member 18 extends from near the proximal end 16 of main tube member 12 in a position and orientation that prevents kinking of the tubing that is connected to the inlet tube member 18 to enable free flow of water or other treating fluid into main tube member 12. Water inlet tube 18 can be designed such that it will maintain a ten degree reverse fluid flow to facilitate the Venturi Effect, namely the reduction in fluid pressure that results when fluid flows through a constricted section of pipe, for elimination purposes. In another exemplary embodiment, the inlet tube member 18 may include a swivel mechanism which is further shown and described with reference to FIG. 8.

Main tube member 12 of rectal speculum 10 may include a distal portion X located near the distal end 14 of main tube member 12 and a proximal portion Y located near the proximal end 16 of main tube member 12. In use, most of the distal portion X of the main tube member 12 is inserted into a patient's rectum while the proximal portion Y of the main tube member 12 remains external to the patient. In accordance with an exemplary embodiment of the soft dual-layer rectal speculum of the present invention, the distal portion X may comprise that portion of the main tube member 12 that includes an inner hard layer and an outer soft layer.

Figure 3:
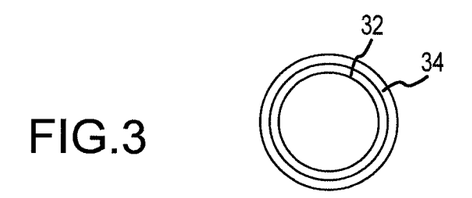
FIG. 3 is a cross-sectional view of the rectal speculum of the present invention taken along lines 3-3, as shown in FIG. 1.

A cross-sectional view of the rectal speculum of the present invention taken along lines 3-3 of FIG. 1 is shown in FIG. 3. FIG. 3 shows a cross section of distal portion X of main tube member 12. Distal portion X of main tube member 12 includes an inner hard layer 32 made of a hard, strong, durable lightweight plastic or polymer material and an outer soft layer 34 made of a soft, pliable material. The inner hard layer 32 may comprise one or more of a polypropylene or a synthetic resin and the outer soft layer 34 may comprise one or more of a polyethylene, a silicone, a soft urethane, a thermoplastic elastomer, or a thermoplastic polyurethane.

The outer soft layer 34 adheres to the inner hard layer 32 and the adhesion of the outer soft layer 34 to the inner hard layer 32 may be performed by one or more techniques including, but not limited to, thermal bonding, chemical bonding, and mechanical bonding. In one exemplary embodiment, the distal portion X of main tube member 12 having inner hard layer 32 and outer soft layer 34 is created by a two step injection molding process where the inner hard layer 32 is molded first and the outer soft layer 34 is molded second such that the outer soft layer 34 adheres to the inner hard layer 32. Further, outer soft layer 34 preferably comprises as many as possible of the following characteristics: soft touch; rubbery feel; excellent colorability; high flow for long, thin-wall parts; adhesion to polypropylene; and good ozone and UV resistance. In addition, outer soft layer 34 may be clear, transparent, or translucent to enable another exemplary embodiment of the soft dual-layer rectal speculum that includes a measurement gauge that is visible through the outer soft layer 34. One example of a material that meets most all of these characteristics for the outer soft layer 34 is STARFLEX P 7012-1001 manufactured by Star Thermoplastic Alloys and Rubbers Inc. located in Broadview, Ill.

Figure 4:
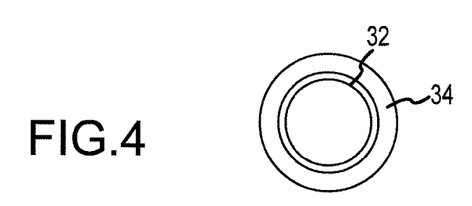
FIG. 4 is a cross-sectional view similar to FIG. 3 showing an alternative embodiment of the two layers which comprise at least a portion of the main tube member of the rectal speculum.
Figure 5:
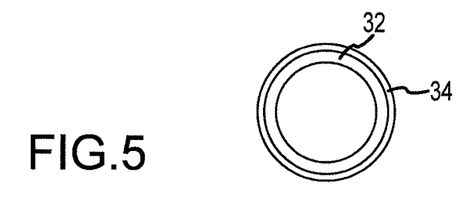
FIG. 5 is a cross-sectional view similar to FIG. 3 showing another alternative embodiment of the two layers which comprise at least a portion of the main tube member of the rectal speculum.

FIG. 3 shows the inner hard layer 32 of distal portion X of main tube member 12 having a same thickness as the outer soft layer 34 of distal portion X of main tube member 12. Inner hard layer 32 and outer hard layer 34 may also comprise other thicknesses depending on the intended use of the soft dual-layer rectal speculum or the patient for which the soft dual-layer rectal speculum will be used. Other exemplary embodiments of the soft dual-layer rectal speculum having various thicknesses for inner hard layer 32 and outer hard layer 34 are shown in FIGS. 4 and 5. FIG. 4 is a cross-sectional view similar to FIG. 3 showing an alternative embodiment of the two layers which comprise at least a portion of the main tube member 12 of the rectal speculum 10. In this embodiment, outer soft layer 34 has a thickness that is greater than inner hard layer 32. FIG. 5 is a cross-sectional view similar to FIG. 3 showing another alternative embodiment of the two layers which comprise at least a portion of the main tube member 12 of the rectal speculum 10. In this embodiment, inner hard layer 32 has a thickness that is greater than outer soft layer 34.

In another exemplary embodiment of the soft dual-layer rectal speculum 10 of the present invention, the distance between the distal portion X of the main tube member 12 and inlet tube member 18 is at least greater than one half of the length of the distal portion X of main tube member 12 to enable waste and fluid lines connected to the soft dual-layer rectal speculum to be further away from a patient during use. This exemplary embodiment can be seen in FIG. 1 where the distance between distal portion X of main tube member 12 and inlet tube member 18 is denoted as length Z and one half the length of distal portion X is denoted as length W. As shown in FIG. 1, length Z is greater than length W. Moreover, in the same or another exemplary embodiment, the soft dual-layer rectal speculum of the present invention is approximately one inch longer in length than current prior art rectal speculums for use in colon hydrotherapy and this additional length is added to the hose connection portion (i.e. the proximal portion Y) of the main tube member 12. This additional length has no impact on the insertion or penetration length into the patient/client and allows the practitioner more access for the insertion procedure. In addition, the added length to proximal portion Y increase patient/client comfort, eliminates possible restrictions due to the physical requirements of the patient/client, and provides added stability during insertion of the soft dual-layer rectal speculum.

The exemplary embodiment of the soft dual-layer rectal speculum shown in FIG. 1 further includes a thumb rest 22 extending outward from the outer surface of the proximal portion Y of main tube member 12 opposite inlet tube member 18. In addition, to assist in retaining the rectal speculum in place during use, the distal portion X of the soft dual-layer rectal speculum of the present invention shown in FIG. 1 includes an annular depression 24 that extends about the speculum for receiving the normally contracted rectal sphincter muscle and annular expansions 26 on opposite sides of the annular depression to prevent axial translation of the rectal speculum as a result of interference with the rectal sphincter muscle.

Figure 2:
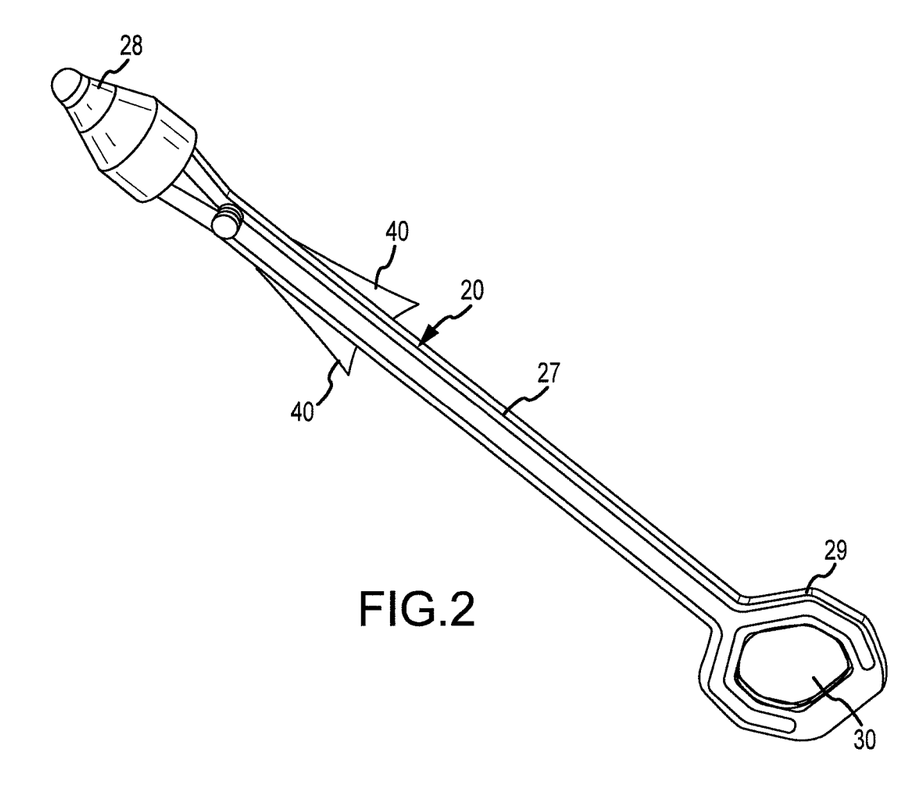
FIG. 2 is a perspective view of an exemplary embodiment of an obturator in accordance with the present invention wherein the obturator fits inside the rectal speculum of the present invention.

FIG. 2 is a perspective view of an exemplary embodiment of an obturator 20 in accordance with the present invention wherein the obturator 20 fits inside the rectal speculum of the present invention to facilitate insertion of the rectal speculum into the patient's rectal canal and lower intestine. Obturator 20 includes an elongated member 27 having a tapered distal end 28 capable of extending through the distal end 14 of main tube member 12 of rectal speculum 10 and a proximal end 29 having a handle portion for assistance in inserting the obturator 20 into the main tube member 12 and removing the obturator 20 from the main tube member 12. Handle portion of proximal end 29 includes an opening 30 for assisting in pushing the obturator 20 into main tube member 12 and removing obturator 20 from main tube member 12. It will be understood by those skilled in the art that the handle portion of proximal end 29 may comprise any number of designs and configurations as long as the handle portion assists a user in inserting and removing the obturator into and out of the main tube member 12 of rectal speculum 10.

Tapered distal end 28 of obturator 20 may comprise a soft pliable material. The soft pliable material may include one or more of a polyethylene, a silicone, a soft urethane, a thermoplastic elastomer, or a thermoplastic polyurethane. Alternatively, tapered distal end 28 of obturator 20 may comprise an inner hard layer (or inner hard member) and an outer soft layer such as those described with reference to the soft dual-layer rectal speculum shown in FIG. 1. The inner hard layer (or member) may comprise one or more of a polypropylene or a synthetic resin and the soft outer layer may comprise one or more of a polyethylene, a silicone, a soft urethane, a thermoplastic elastomer, or a thermoplastic polyurethane. In addition, the elongated member 27 of obturator 20 may include one or more stabilizing flanges 40 to provide more stability during the insertion process.

Figure 6:
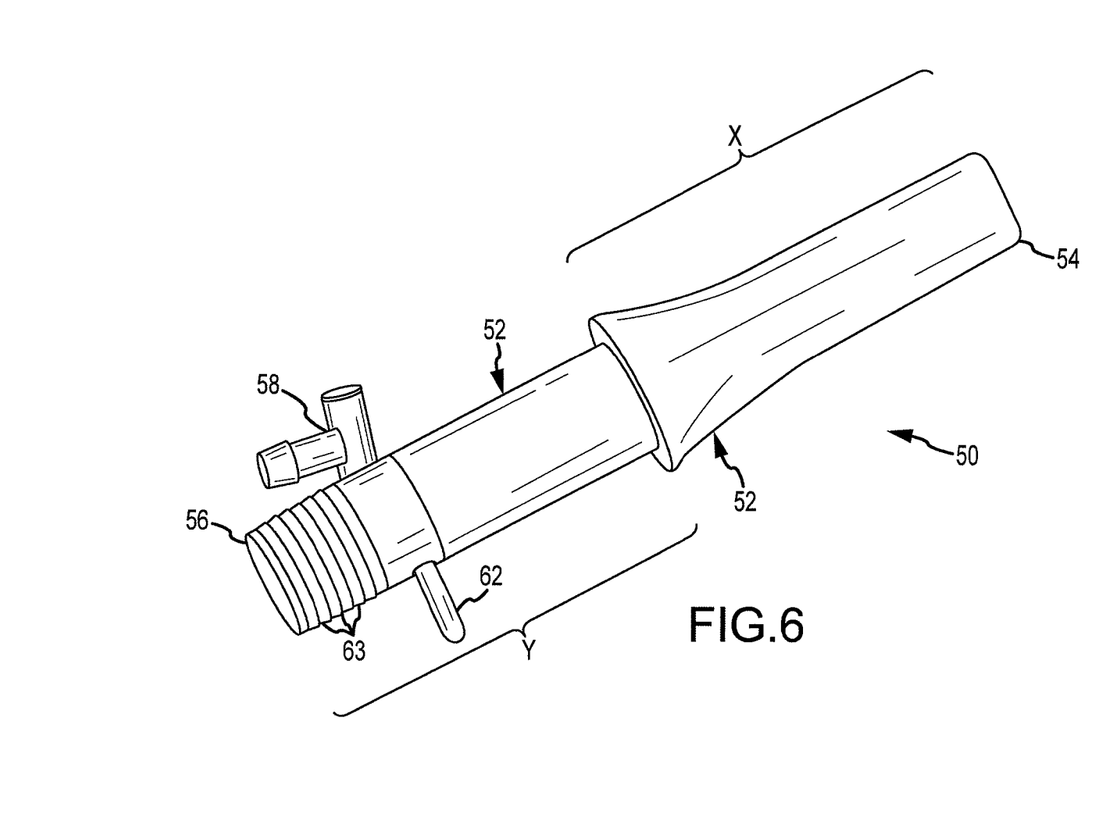
FIG. 6 is a perspective view of another exemplary embodiment of a rectal speculum in accordance with the present invention.

FIG. 6 is a perspective view of another exemplary embodiment of a rectal speculum in accordance with the present invention. Soft dual-layer rectal speculum 50 includes a main tube member 52 having a distal end 54 for insertion into a patient's rectum and a proximal end 56 for connection to a waste removal hose. At least a portion of the main tube member 52 includes an inner hard layer and an outer soft layer as previously described with reference to FIG. 1 and as previously shown and described with reference to FIGS. 3-5. Rectal speculum 50 also includes an inlet tube member 58 for directing fluids into the main tube member 52.

Inlet tube member 58 intersects main tube member 52 near the proximal end 56 of main tube member 52 and inlet tube member 58 has a diameter that is smaller than the diameter of main tube member 52. Inlet tube member 58 extends from near the proximal end 56 of main tube member 52 in a position and orientation that prevents kinking of the tubing that is connected to the inlet tube member 58 to enable free flow of water or other treating fluid into main tube member 52. Water inlet tube 58 can be designed such that it will maintain a ten degree reverse fluid flow to facilitate the Venturi Effect, namely the reduction in fluid pressure that results when fluid flows through a constricted section of pipe, for elimination purposes.

Main tube member 52 of rectal speculum 50 may include a distal portion X located near the distal end 54 of main tube member 52 and a proximal portion Y located near the proximal end 56 of main tube member 52. In use, most of the distal portion X of the main tube member 52 is inserted into a patient's rectum while the proximal portion Y of the main tube member 52 remains external to the patient. In accordance with an exemplary embodiment of the soft dual-layer rectal speculum of the present invention, the distal portion X may comprise that portion of the main tube member 52 that includes an inner hard layer and an outer soft layer.

The inner hard layer and outer soft layer of distal portion X of main tube member 52 may comprise any of those materials previously discussed with reference to the inner hard layer and outer soft layer of the soft dual-layer rectal speculum shown and described in FIG. 1. In addition, the thicknesses of the inner hard layer and the outer soft layer may comprise any of those embodiments previously discussed with reference to FIGS. 3-5. Moreover, adhesion of the outer soft layer to the inner hard layer may be performed by any of those methods previously described with reference to the soft dual-layer rectal speculum shown and described in FIG. 1.

Like the soft dual-layer rectal speculum shown and described in FIG. 1, the exemplary embodiment of the soft dual-layer rectal speculum shown in FIG. 6 also includes a thumb rest 62 extending outward from the outer surface of the proximal portion Y of main tube member 52 opposite inlet tube member 58. Thumb rest 62 assists in keeping the rectal speculum 50 steady while the obturator 20 is removed and a waste removal hose is attached to the proximal end 56 of main tube member 52. When removing obturator 20 from main tube member 52 and attaching the waste removal hose, a technician or physician can grasp the speculum 50 between his or her thumb and index finger and place the distal side of the thumb rest 62 against the back of his or her thumb. The resulting steady force exerted by the hand resists movement of the speculum 50 during removal of the obturator and attachment of the waste removal hose. The soft dual-layer rectal speculum shown in FIG. 6 also includes one or more ribs 63 at the proximal end 56 of main tube member 52 to allow for better cohesion when the waste removal hose is connected to the rectal speculum 50 and to prevent leaking of waste at the proximal end 56 of rectal speculum 50.

Figure 7:
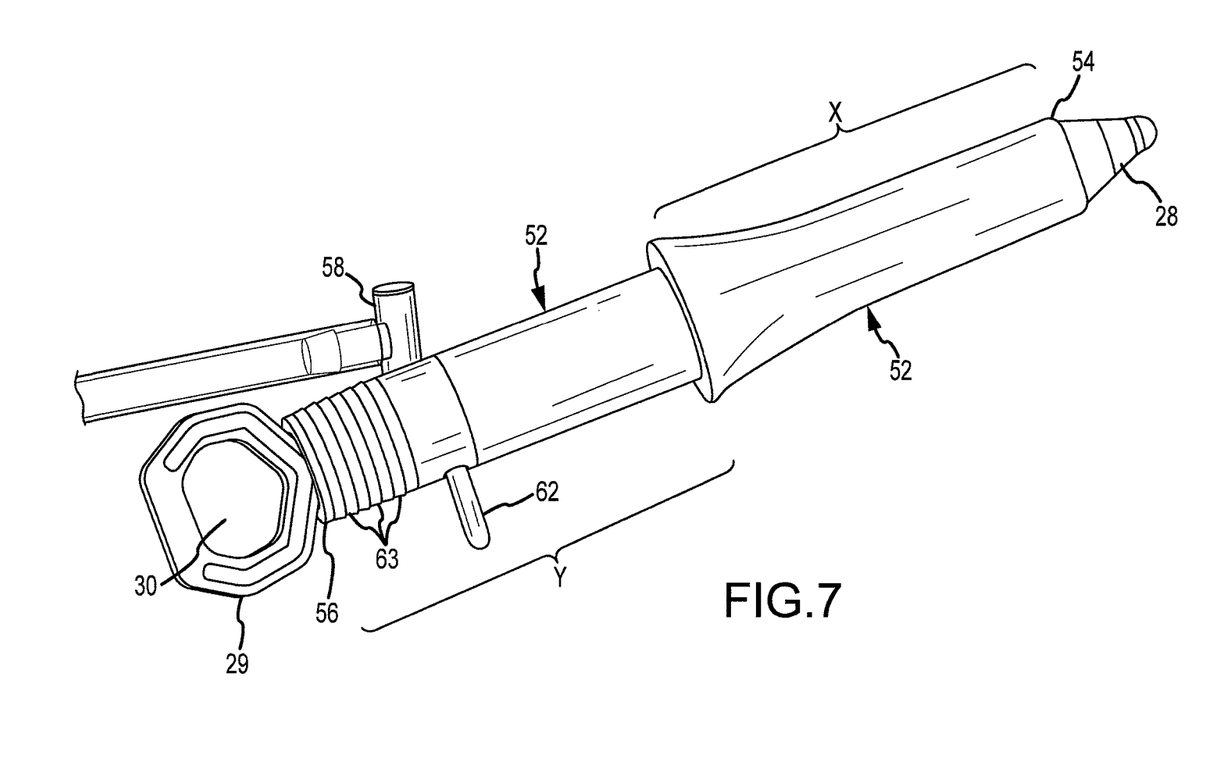
FIG. 7 is a perspective view of a rectal speculum assembly in accordance with the present invention showing the obturator depicted in FIG. 2 positioned within the exemplary rectal speculum shown in FIG. 6 and a fluid source connected to the inlet tube member of the rectal speculum.

A perspective view of a rectal speculum assembly in accordance with the present invention showing the obturator depicted in FIG. 2 positioned within the exemplary rectal speculum shown in FIG. 6 and a fluid source connected to the inlet tube member of the rectal speculum is shown in FIG. 7. The tapered distal end 28 of the obturator 20 and most of the distal portion X of main tube member 52 of speculum 50 are inserted into a patient's rectum. The obturator 20 is then removed from the rectal speculum 50 by utilizing the handle portion (in this case opening 30) of proximal end 29 of obturator 20 to pull obturator 20 out of rectal speculum 50. Water or treating fluid is then injected through inlet tube member 58 and resulting waste exits the rectal speculum 50 at the proximal end 56 of the speculum 50 which is attached to a waste removal hose.

Figure 8:
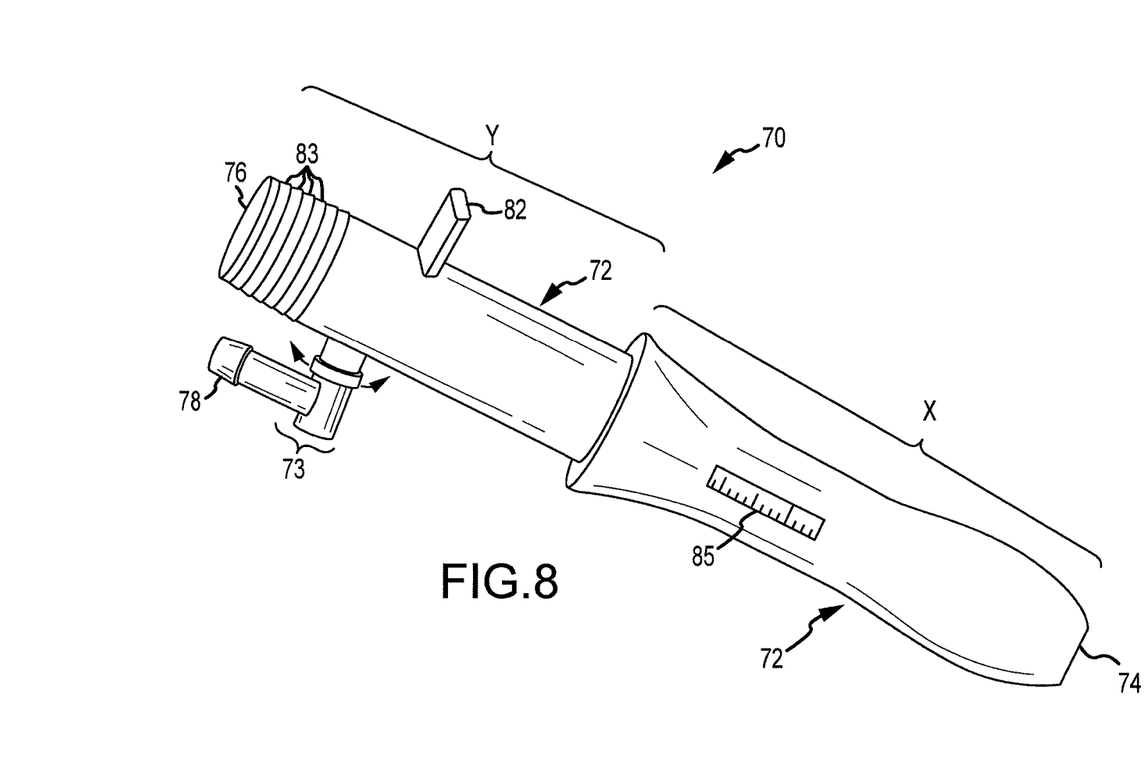
FIG. 8 is yet another exemplary embodiment of a rectal speculum in accordance with the present invention.

FIG. 8 is yet another exemplary embodiment of a rectal speculum 70 in accordance with the present invention. The soft dual-layer rectal speculum 70 shown in FIG. 8 is almost identical to the soft dual-layer rectal speculum 10 shown in FIG. 1 with three exceptions—the inclusion of a measurement gauge visible through the outer soft layer of the distal portion X of the main tube member, the inclusion of a swivel mechanism in the inlet tube member, and the addition of one or more ribs at the proximal end of the main tube member.

Rectal speculum 70 includes a main tube member 72 having a distal end 74 for insertion into a patient's rectum and a proximal end 76 for connection to a waste removal hose. At least a portion of the main tube member 72 includes an inner hard layer and an outer soft layer as further shown and described with reference to FIG. 1 and as previously shown and described with reference to FIGS. 3-5. Rectal speculum 70 also includes an inlet tube member 78 for directing fluids into the main tube member 72.

Inlet tube member 78 intersects main tube member 72 near the proximal end 76 of main tube member 72 and inlet tube member 78 has a diameter that is smaller than the diameter of main tube member 72. Inlet tube member 78 includes a swivel mechanism 73 which is capable of enabling a fluid line connected to the inlet tube member 78 to rotate in relation to the main tube member 72. Swivel mechanism 73 provides a 360 degree access allowing the water or treating fluid hose to be repositioned during the course of the treatment to facilitate the needs, physical requirements, and comfort of the patient/client while providing the practitioner with the flexibility to manage the treatment session for optimum results. Swivel mechanism 73 also prevents the water or treating fluid line from kinking and prevents back flow to the pressure gauge which can result in the gauge blowing at the diaphragm.

Main tube member 72 of rectal speculum 70 may include a distal portion X located near the distal end 74 of main tube member 72 and a proximal portion Y located near the proximal end 76 of main tube member 72. In use, most of the distal portion X of the main tube member 72 is inserted into a patient's rectum while the proximal portion Y of the main tube member 72 remains external to the patient. In accordance with an exemplary embodiment of the soft dual-layer rectal speculum of the present invention, the distal portion X may comprise that portion of the main tube member 72 that includes an inner hard layer and an outer soft layer.

Then inner hard layer and outer soft layer of distal portion X of main tube member 72 may comprise any of those materials previously discussed with reference to the inner hard layer and outer soft layer of the soft dual-layer rectal speculum shown and described in FIG. 1. In addition, the thicknesses of the inner hard layer and the outer soft layer may comprise any of those embodiments previously discussed with reference to FIGS. 3-5. Moreover, adhesion of the outer soft layer to the inner hard layer may be performed by any of those methods previously described with reference to the soft dual-layer rectal speculum shown and described in FIG. 1.

Like the soft dual-layer rectal speculum shown and described in FIGS. 1 and 6, the exemplary embodiment of the soft dual-layer rectal speculum shown in FIG. 8 also includes a thumb rest 82 extending outward from the outer surface of the proximal portion Y of main tube member 72 opposite inlet tube member 78. The soft dual-layer rectal speculum shown in FIG. 8 also includes one or more ribs 83 at the proximal end 76 of main tube member 72 to allow for better cohesion when the waste removal hose is connected to the rectal speculum 70 and to prevent waste from leaking at the proximal end 76 of rectal speculum 70. In addition, the distal portion X of the main tube member 72 of rectal speculum 70 includes a measurement gauge 85 that is visible through the outer soft layer of the distal portion X. In this exemplary embodiment, the outer soft layer is clear, transparent, or translucent so that measurement gauge 85 can be read through the outer soft layer. Measurement gauge 85 may be imprinted or tooled into the inner hard layer of distal portion X prior to adhering the outer soft layer to the inner hard layer. The gauge markings will assist the practitioner by providing an accurate insertion measurement to facilitate the comfort of the patient/client. The measurement gauge markings will not be felt through the outer soft layer of the speculum.

The detailed description of exemplary embodiments of the invention herein show various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure. It will be understood by those skilled in the art that all or some of the main tube member of the rectal speculum includes and inner hard layer and an outer soft layer as long as at least a portion of the main tube member includes an inner hard layer and an outer soft layer.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning. The terms "client" and "patient" are used interchangeably throughout the specification as are the terms "practitioner", "physician", and "technician".

The invention claimed is:

1. A dual-layer rectal speculum for use with colon hydrotherapy comprising:
    a main tube member having a distal end for insertion into a patient's rectum and a proximal end tor connection to a waste removal hose wherein at least a portion of the main tube member comprises an inner hard layer and an outer soft layer that is transparent; and
    an inlet tube member for directing fluids into the main tube member wherein the inlet tube member has a diameter less than a diameter of the main tube member and further includes a swivel mechanism capable of enabling a fluid line connected to the inlet tube member to rotate in relation to the main tube member.

2. The dual-layer rectal speculum of claim 1 wherein the main tube member further comprises a distal portion located near the distal end of the main tube member and a proximal portion located near the proximal end of the main tube member.

3. The dual-layer rectal speculum of claim 2 wherein the distal portion of the main tube member comprises an inner hard layer and an outer soft layer.

4. The dual-layer rectal speculum of claim 3 wherein the outer soft layer adheres to the inner hard layer.

5. The dual-layer rectal speculum of claim 4 wherein adhesion of the outer soft layer to the inner hard layer is performed by at least one of thermal bonding, chemical bonding, and mechanical bonding.

6. The dual-layer rectal speculum of claim 3 wherein the distal portion of the main tube member further comprises an annular depression.

7. The dual-layer rectal speculum of claim 6 wherein the distal portion further comprises annular expansions on opposite sides of the annular depression.

8. The dual-layer rectal speculum of claim 3 wherein the main tube member further comprises a measurement gauge visible through the outer soft layer.

9. The dual-layer rectal speculum of claim 8 wherein the measurement gauge is imprinted within, or tooled into, the inner hard layer of the main tube member.

10. The dual-layer rectal speculum of claim 3 wherein the inner hard layer comprises at least one of a polypropylene and a synthetic resin and the outer soft layer comprises at least one of a polyethylene, a silicone, a soft urethane, a thermoplastic elastomer, and a thermoplastic polyurethane.

11. The dual-layer rectal speculum of claim 2 wherein the inlet tube member is located on the proximal portion of the main tube member near the proximal end of the main tube member.

12. The dual-layer rectal speculum of claim 1 wherein the portion of the main tube member comprising the inner hard layer and the outer soft layer is created by a two step molding process where the inner hard layer is molded first and the outer soft layer is molded second such that the outer soft layer adheres to the inner hard layer.

13. The dual-layer rectal speculum of claim 1 wherein the inner hard layer comprises at least one of a polypropylene and a synthetic resin and the outer soft layer comprises at least one of a polyethylene, a silicone, a soft urethane, a thermoplastic elastomer, and a thermoplastic polyurethane.

14. The dual-layer rectal speculum of claim 1 wherein the main tube member further comprises a measurement gauge visible through the outer soft layer.

15. The dual-layer rectal speculum of claim 1 further comprising a thumb rest extending outward from an outer surface of the main tube member opposite the inlet tube member.

16. The dual-layer rectal speculum of claim 1 wherein the proximal end of the main tube member includes one or more ribs for securing the proximal end of the main tube member to a waste removal hose.

17. The dual-layer rectal speculum of claim 1 wherein the inlet tube member intersects the main tube member near the proximal end of the main tube member.

18. The dual-layer rectal speculum of claim 11 wherein the distance between an end of the distal portion of the main tube member opposite the distal end and the inlet tube member is at least greater than one half of the length of the distal portion of the main tube member to enable waste and fluid lines connected to the dual-layer rectal speculum to be further away from a patient during use.

19. A rectal speculum assembly for use with colon hydrotherapy comprising:
   a main tube member having a distal end for insertion into a patient's rectum and a proximal end for connection to a waste removal hose wherein at least a portion of the main tube member comprises an inner hard layer and an outer soft layer that is transparent;
   an inlet tube member for directing fluids into the main tube member wherein the inlet tube member has a diameter less than a diameter of the main tube member and further includes a swivel mechanism capable of enabling a fluid line connected to the inlet tube member to rotate in relation to the main tube member, and
   an obturator removably positioned within the main tube member of the rectal speculum for facilitating insertion of the rectal speculum in a patient's rectum wherein the obturator comprises an elongated member having a tapered distal end capable of extending through the distal end of the main tube member and a proximal end having a handle portion for assistance in inserting the obturator into the main tube member and removing the obturator from the main tube member.

20. The rectal speculum assembly of claim 19 wherein the tapered distal of the obturator comprises a soft pliable material.

21. The rectal speculum assembly of claim 20 wherein the tapered distal end comprises at least one of a polyethylene, a silicone, a soft urethane, a thermoplastic elastomer, and a thermoplastic polyurethane.

22. The rectal speculum of claim 20 wherein the elongated member comprises one or more stabilizing flanges.

23. The rectal speculum assembly of claim 19 wherein the tapered distal end of the obturator comprises an inner hard layer and an outer soft layer.

24. The rectal speculum assembly of claim 23 wherein the inner hard layer comprises at least one of a polypropylene and a synthetic resin and the outer soft layer comprises at least one of a polyethylene, a silicone, a soft urethane, a thermoplastic elastomer, and a thermoplastic polyurethane.

25. The rectal speculum of claim 23 wherein the elongated member comprises one or more stabilizing flanges.

26. A dual-layer rectal speculum for use with colon hydrotherapy comprising:
   a main tube member comprising a distal portion having a distal end for inserting into a patient's rectum and a proximal portion having a proximal end for connection to a waste removal hose wherein the distal portion comprises and inner hard layer and an outer soft layer; and
   an inlet tube member for directing fluids into the proximal portion of the main tube member wherein the distance between an end of the distal portion opposite the distal end and the inlet tube member is greater than one half of the length of the distal portion of the main tube member and further includes a swivel mechanism capable of enabling a fluid line connected to the inlet tube member to rotate in relation to the main tube member.

* * * * *